United States Patent
Wieters et al.

(10) Patent No.: US 10,524,649 B2
(45) Date of Patent: Jan. 7, 2020

(54) VIDEO ENDOSCOPE

(71) Applicant: OLYMPUS WINTER & IBE GMBH, Hamburg (DE)

(72) Inventors: Martin Wieters, Barsbuettel (DE); Thorsten Juergens, Hamburg (DE); Jens Schnitger, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 351 days.

(21) Appl. No.: 15/358,546

(22) Filed: Nov. 22, 2016

(65) Prior Publication Data

US 2017/0071462 A1 Mar. 16, 2017

Related U.S. Application Data

(63) Continuation of application No. PCT/EP2015/061144, filed on May 20, 2015.

(30) Foreign Application Priority Data

May 26, 2014 (DE) .......... 10 2014 209 980

(51) Int. Cl.
*A61B 1/12* (2006.01)
*A61B 1/05* (2006.01)

(52) U.S. Cl.
CPC .......... *A61B 1/128* (2013.01); *A61B 1/051* (2013.01); *A61B 1/12* (2013.01)

(58) Field of Classification Search
CPC .. A61B 1/05; A61B 1/051; A61B 1/12; A61B 1/128
See application file for complete search history.

(56) References Cited

U.S. PATENT DOCUMENTS

| | | |
|---|---|---|
| 2010/0033559 A1 | 2/2010 | Yasunaga |
| 2011/0211053 A1 | 9/2011 | Nakayama |
| 2011/0249106 A1 | 10/2011 | Makino et al. |
| 2014/0371530 A1 | 12/2014 | Wieters et al. |

FOREIGN PATENT DOCUMENTS

| | | |
|---|---|---|
| DE | 102012202133 A1 | 8/2013 |
| EP | 2 644 084 A1 | 10/2013 |
| EP | 2 767 213 A1 | 8/2014 |
| JP | 2012-055489 A | 3/2012 |
| JP | 2013-081656 A1 | 5/2013 |
| JP | 2013-198642 A | 10/2013 |
| WO | 2010/064506 A1 | 6/2010 |
| WO | WO 2010064506 A1 | 6/2010 |

OTHER PUBLICATIONS

International Search Report dated Jul. 30, 2015 issued in PCT/EP2015/061144.
Japanese Office Action dated Jun. 26, 2018 in Japanese Patent Application No. 2016-569733.

*Primary Examiner* — Aaron B Fairchild
(74) *Attorney, Agent, or Firm* — Scully, Scott, Murphy & Presser, P.C.

(57) ABSTRACT

A video endoscope including: a shank; an image-recording device arranged in a distal region of the shank; a flexible circuit board electrically connected to an image-recording device; and a cooling element; wherein the flexible circuit board rests on the cooling element and at least portions of an exterior of the cooling element fit an inner contour of the shank in a stress-free manner.

10 Claims, 2 Drawing Sheets

VIDEO ENDOSCOPE

CROSS-REFERENCE TO RELATED APPLICATION

The present application is a continuation of PCT/EP2015/061144 filed on May 20, 2015, which is based upon and claims the benefit to DE 10 2014 209 980.3 filed on May 26, 2014, the entire contents of each of which are incorporated herein by reference.

BACKGROUND

Field

The present application relates to a video endoscope comprising an image-recording device which is arranged in the distal region of the video endoscope in a shank, whereby the image-recording device is electrically connected to a flexible circuit board.

Prior Art

DE 10 2012 202 133 A1 describes an electrical connector for a video endoscope with a hermetically sealed video unit in a shank of the endoscope, a corresponding video endoscope and a procedure to produce an electrical connection in a video endoscope. The electrical connection piece, includes an at least partially flexible printed circuit board having conductive tracks, wherein the printed circuit board has a base surface with openings for contact pins, a hermetic feedthrough, and a flexible first arm and a flexible second arm that branch off in opposite directions from the base surface, wherein the first arm and the second arm each have a flat end surface at the respective ends facing away from the base surface, wherein the conductive tracks extend between the openings on the base surface and electrical contacting surfaces in the end surfaces.

To improve the image quality of video endoscopes, it is advisable to use a cooling element that discharges heat generated by the electronic components. This prevents dark noise and also prevents the misalignment of the optical components.

SUMMARY

It is an object to provide an improved video endoscope with an image-recording device, whereby the device lifetime is also increased.

Such object can be achieved with the use of a video endoscope comprising an image-recording device which is arranged in the distal region of the video endoscope in a shank, whereby the image-recording device is electrically connected to a flexible circuit board, whereby the flexible circuit board rests on a cooling element, whereby at least portions of the exterior of the cooling element fit an inner contour of the shank in a stress-free manner.

The addition of the cooling element, whereby at least portions of its exterior fit an inner contour of the shank in a stress-free manner, allows very good heat transfer to the shank, thereby increasing cooling. Furthermore, as the cooling element is large, or has an appropriately large surface area, which is fitted in portions to the inner contours of the shank in a stress-free manner, a larger surface can be provided for heat dissipation. The stress-free fitting of the exterior of the cooling element to the internal contours of the shank also ensures that the electrical junction, for example soldering joints of electrical components soldered to a substrate, such as a flexible circuit board, and electrical junctions to the image-recording device can be kept stress-free, or essentially stress-free. This increases the service life of the video endoscope.

A settable distance can be provided between the exterior of the cooling element and the internal contour of the shank. Providing a settable distance, it is very easy to allow stress-free fitting. The settable distance can be in the range of 0.1 to 0.5 mm, such as between 0.2 and 0.3 mm Stress-free, for the purpose of this disclosure, is understood as avoiding mechanical stress. At least portions of the exterior of the cooling element can fit an inner contour of the shank in a stress-free manner. The shank can be designed as a cylindrical tube. In this case, at least portions of the exterior contours of the cooling element can be cylindrical or circular in cross section.

A flexible casting material can be placed between the internal contour of the shank and the exterior of the cooling element. The casting material can be heat conducting and electrically insulating. This may be a liquid, curable polymer, such as silicone. To provide thermal conductivity the liquid, hardened polymer that can be still flexible when hardened, can be filled with boron nitride. Other applicable filling materials are aluminum nitrite, silicon carbide, aluminum oxide, silicon dioxide or silicon nitrite, to increase the heat conductivity of the polymer, such as silicone.

The heat of the components is very effectively dissipated if at least one heat-generating electrical component, applied to the flexible circuit board, is in contact with the cooling element. This can be a CCD chip, but can also be a driver chip or transistors, used to run the image-recording device. The components can be in the form of SMD components. At least one component or several components can be in contact with the cooling element.

The flexible circuit board can be made of at least one first flexible circuit board and a second flexible circuit board, electrically connected with each other in the region of the cooling element, such as by being soldered. In this case, the first flexible circuit board, which can be short in configuration, can be configured to hold the image-recording device or a part of the image-recording device. This facilitates handling when installing the image-recording device in the video endoscope, or when assembling the video endoscope. Then, for instance, a prefabrication of a CCD chip can be provided on the first flexible circuit board. This means that generally very mechanically small electrical contacts can thus be soldered onto a short, flexible circuit board by machine. When fitting the video endoscope, the individuals responsible for the assembly can then provide slightly larger soldering contacts, so as to electrically connect the first flexible circuit board with the second flexible circuit board.

The first flexible circuit board can be configured to hold the image-recording device, and fitted further to the distal end than the second flexible circuit board.

This allows good heat contact transfer when the first flexible circuit board is bonded with the cooling element.

To allow precise assembly and to facilitate that the assembly of the flexible circuit board is as mechanically stress-free as possible, the cooling element can include a side guide for the flexible circuit board. In this case both the first flexible circuit board and the second flexible circuit board can have a side guide. It is possible that only one of the two flexible circuit boards has a side guide.

The cooling element can have a side guide for the second flexible circuit board, whereby the guide can be configured as a groove, to configure an additional guide for the second flexible circuit board perpendicular to the side guide. This limits the height adjustment of the second flexible circuit board. The grove can be used to clamp the second flexible circuit board in place. The second flexible circuit board can be clamped into the groove with enough stress to ensure that the second flexible circuit board rests on the first circuit board at the distal end of the second circuit board. In this case the first flexible circuit board can be between the second flexible circuit board and the cooling element.

The cooling element can be at least partially, or fully, electrically insulated. With this configuration there are no circumstances in which there can be short circuits in the electrical connections.

An electrically insulating coating of the cooling element can be provided. The cooling element can, for instance, be coated with an electrically insulating coating, e.g. an electron sputter coating or laser ablation. Silicon oxide or boron nitride or sapphire can be used for a coating of, for example, of a cooling element made of copper. The cooling element can be made of aluminum, whereby the surface of the cooling element can be electrically insulated by hard anodizing. This ensures not only an electrical insulation of the coating of the cooling element or the surface of the cooling element, but also provides very good abrasion resistance, so it can be assumed that a permanent insulating surface of the cooling element can be assured.

The internal contours of the shank can follow the shape at least in portions or approximately follow the shape of the external contour of a portion of the cooling element. The internal contour of the shank follows or at least approximately follows the external contours of a portion of the cooling element in a cross section that is transverse, such as at right angles, to the longitudinal axis of the shank. This allows close adjustment of the cooling element in the shank, to allow efficient heat transfer from the cooling element to the shank.

The exterior of the cooling element can be circular and have a radius essentially equivalent to the radius of the internal contour of the shank.

The cooling element can be completely molded into the shank with a flexible casting material. The shank can be an internal shank of the video endoscope. The image-recording device can be in a hermetically sealed space in the video endoscope.

The video endoscope may have one image-recording device. However, a video endoscope having at least two image-recording devices, whose light sensitive surfaces are orthogonally aligned to each other can also be provided. For instance, two CCD chips may be included in the configuration whose image-recording surfaces are orthogonal to each other. The image-recording surfaces of the CCD chips may be adjacent to the surfaces of prisms. At the distal end of the video endoscope suitable lenses or a suitable lens may be arranged between the prism or prisms.

At least in portions, an internal contour or an interior of the shank can be adjusted to the external contour or exterior of the cooling element. This can be adjusted so that the external contours of the cooling element follow the shape or approximately follow the shape of the internal contour of the shank, such as in portions. The portion may be a portion long the longitudinal axis. The portion can be an alternative or can complement a portion transverse to the longitudinal axis of the shank.

The cooling element can be wing-shaped and the wings may have an external contour or exterior that fits the internal contour of the shank. In the case that the shank is circular and thus the internal contour of the shank is circular, the exterior of the cooling element can be circular in segments and thus be adjusted to the internal contours of the shank, which can be of complementary shape.

Further features will become apparent from the description of embodiments together with the claims and the included drawings. Embodiments can fulfill individual characteristics or a combination of several characteristics.

BRIEF DESCRIPTION OF THE DRAWINGS

An embodiment are described below without restrictions to the general inventive concept, based on the exemplary embodiment, with referencing the drawings, whereby all details that are not explained in detail in the text are explicitly illustrated in the drawings.

DETAILED DESCRIPTION

Figure 1:
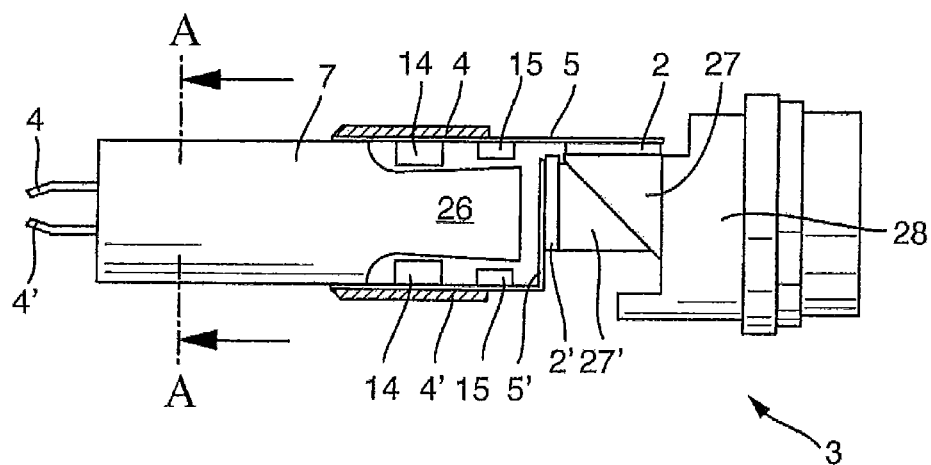
FIG. 1 illustrates a lateral view of a part of the video endoscope.

FIG. 1 shows a part of the video endoscope 1. The device is configured for two image-recording devices 2 and 2', in this case in the form of CCD chips, attached to a first flexible circuit board 5 or 5'. The image-recording devices 2, 2' are each configured adjacent to a prism 27 or 27'. The prisms 27, 27' can be configured to transmit an image from an objective not shown, that is arranged in the distal region 3 of the video endoscope 1 in an optical system housing 28, to the CCD chip or CCD sensors 2, 2'.

It is, for example, possible to arrange filters between the CCD sensors 2, 2' and the respective prisms 27, 27', to provide filtered images for the variety of application purposes. Generally, an internal shank or internal tube is arranged to prove a hermetic seal with the optical system housing 28. This is not illustrated in FIG. 1, but is as reference number 10 in FIG. 2.

The flexible circuit boards 5, 5', which can also be described as CCD tabs or flexboards, are relatively short and in the illustration of FIG. 1 maximally reach to the left end of a cooling element 7 and at the distal end of the endoscope 1 to the image-recording devices 2, 2'. Electronic components 14, 15 are secured to the flexible circuit boards 5 and 5' which can be in heat contact with the cooling element 7. The heat contact can be created so that, as in the example of the electronic components 14, the surfaces of these components are in contact with the cooling element 7. Furthermore, it is possible, with a heat-conducting, but electrically insulated, casting component, which can be elastic, to provide good heat contact between the electronic component 15 and the cooling element 7. The flexible circuit board 5 is relatively straight in this configuration example. The flexible circuit board 5' is essentially perpendicularly angled in the region of the image-recording device 2'. It is also possible to only configure one image-recording device 2 or 2' and to configure corresponding electronic components on the then designated flexible circuit board 5 or 5'.

The flexible circuit boards 4, 4' resting on the flexible circuit boards 5 or 5' are configured to conduct the electrical contacts from the distal end of the video endoscope to the proximal end. This flexible circuit board 4, 4', which must be flexible at least in portions, therefore rests partially on the first flexible circuit board 5, 5'. An electrical contact, for example a solder, of the electric cables is then created, for example, in the contact area 29 or 30. These are shown in FIG. 3.

Figure 3:
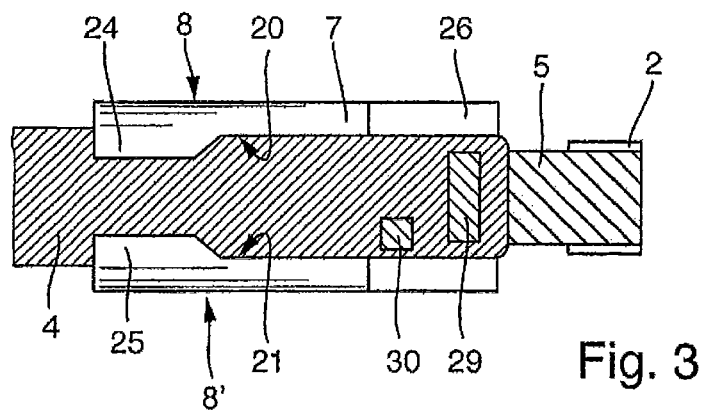
FIG. 3 illustrates a schematic plan view of a part of the illustration of the figure of a part of the video endoscope from FIG. 1.

FIG. 3 shows a schematic plan view of a part of the video endoscope 1, shown in FIG. 1.

FIG. 1 also shows that the cooling element 7 is illustrated as a wedge 26 in FIG. 1 on the right, i.e. towards the distal region 3. In the region of the wedge, space is provided accordingly for electronic components. In the region of the cooling element 7 in the direction of the proximal end, viewed from wedge 26, a space above and behind an internal shank not shown in FIG. 1 is provided to place a casting compound.

Figure 2:
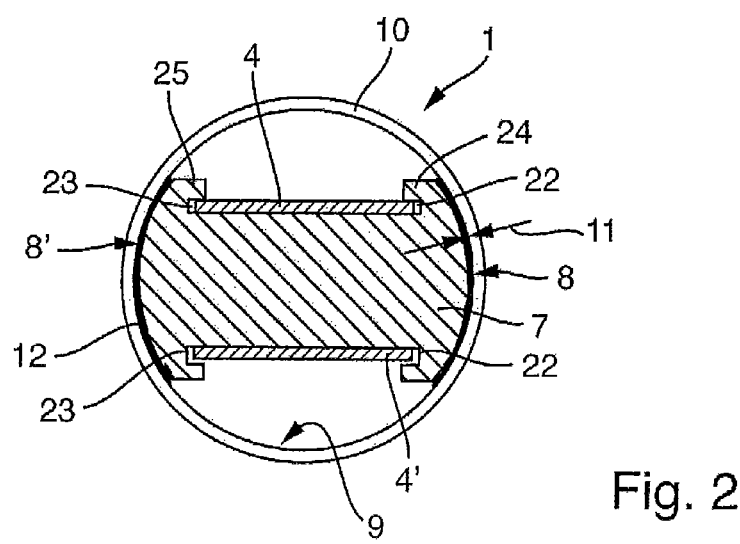
FIG. 2 illustrates a schematic cross sectional view along A-A from FIG. 1.

FIG. 2 schematically illustrates a cross section along the A-A line from FIG. 1. This shows the space between the cooling element 7 and the shank 10 upwards and downwards. It also shows that the cooling element 7 has a wing-like configuration to the sides. The wings have an external contour or exterior that fits the internal contour 9 of the shank 10. In this case the shank is circular in cross section and therefore the internal contour 9 of the shank 10 is circular. The exterior 8, 8' of the cooling element 7 is circular and therefore adjusted to the internal contour 9 of the shank 10. The internal contour 9 of the shank and the exterior 8, 8' of the cooling element are therefore approximately of complementary shape.

The exterior 8, 8' of the cooling element 7 is fitted stress-free to the internal contour 9 of the shank 10. A predefined distance is therefore assigned, indicated by the two arrows 11 in FIG. 2. At this distance casting material 12 can be placed, to allow very efficient thermal conductivity from the cooling element 7 to the shank 10, when the cooling element 7 is inserted largely stress-free into the shank 10.

To further reduce the stress and to facilitate assembly, a side guide 20 or 21 is provided for the flexible circuit board. This is illustrated in FIG. 3. The flexible circuit board 4 can therefore be very efficiently and accurately installed. A side guide can also be configured for the circuit board 5 or 5' (not shown). It is hidden in the plan view of the flexible circuit board 4 in FIG. 3.

A groove 22, 23 is provided, into which the second flexible circuit board 4, 4' and/or the first flexible circuit board 5 can be inserted, so that it is possible to guide from above. The groove can be configured so that the circuit board 4, 4' and/or 5, 5' can be clamped into the groove. To configure a groove of this kind, the cooling element 7 includes a suitable terminal cover 24, 25.

The cooling element can be constructed partially cylindrical. Since the configuration of FIG. 1 permits the cooling element to be very large in configuration, very efficient heat dissipation of the electronic components 14, 15 and the CCD sensors 2, 2' can be achieved. The gap 11 is configured between the cooling element 7 and the shank 10, to allow for tolerances and assembly variances. This reduces the force exerted on the CCD sensors 2, 2'. The use of a flexible casting compound or a flexible material in the space formed in the shank 10 between the shank 10 and the cooling element 7, can correct later positional deviations caused, for example, by thermal or mechanical stress or forces. Since the configuration of FIG. 1 significantly enlarges the surface over which heat is dissipated to the environment, the temperature of the CCD sensors 2, 2' and also of the electronic components 14, 15 is reduced. At least one electronic component is bonded or molded to the cooling element 7. To facilitate assembly, both the first flexible circuit board and the second flexible circuit board are guided or inserted into the corresponding side guides or into the corresponding grooves.

In the drawings, the same or similar types of elements and/or parts are provided with the same reference numbers so that a re-introduction is omitted.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE NUMBERS

1 Video endoscope
2,2' CCD sensor
3 Distal area
4,4' Flexible circuit board
5,5' Flexible circuit board
7 Cooling element
8,8' Exterior
9 Internal contour
10 Shank
11 Distance
12 Casting material
14 Electronic component
15 Electronic component
20 Side guide
21 Side guide
22 Groove
23 Groove
24 Terminal cover
25 Terminal cover
26 Wedge
27,27' Prism
28 Optical system housing
29 Contact area
30 Contact area

What is claimed is:

1. A video endoscope comprising:
a shank;
an image-recording device arranged in a distal region of the shank;
a flexible circuit board electrically connected to the image-recording device; and
a cooling element;
wherein
the flexible circuit board rests on the cooling element and at least portions of an exterior of the cooling element fit an inner contour of the shank in a stress-free manner;
the flexible circuit board comprises at least a first flexible circuit board and a second flexible circuit board, the at least first flexible circuit board and second flexible circuit board being electrically connected to each other in the region of the cooling element, one or more of the first and the second flexible circuit boards having a first edge and a second edge on opposing sides of the one or more of the first and the second flexible circuit boards;
the cooling element has first and second grooves to secure the first and second edges, respectively, of the one or more of the first and the second flexible circuit boards to the cooling element; and
the one or more of the first and the second flexible circuit boards is disposed in the first and second grooves such that a surface of the one or more of the first and the second flexible circuit boards between the first and second edges contacts a corresponding surface of the cooling element.

2. The video endoscope according to claim 1, wherein a settable distance is provided between the exterior of the cooling element and the internal contour of the shank.

3. The video endoscope according to claim 1, further comprising a flexible casting material placed between the inner contour of the shank and the exterior of the cooling element.

4. The video endoscope according to claim 1, further comprising at least one heat-generating electronic component arranged on the at least first flexible circuit board and second flexible circuit board, the at least one heat-generating electronic component being in contact with the cooling element.

5. The video endoscope according to claim 1, wherein the first flexible circuit board is configured to hold the image-recording device and is arranged further towards the distal end than the second flexible circuit board.

6. The video endoscope according to claim 5, wherein the first flexible circuit board is bonded to the cooling element.

7. The video endo scope according to claim 1, wherein the cooling element is electrically insulated at least in portions.

8. The video endoscope according to claim 7, wherein the cooling element is electrically insulated as a whole.

9. The video endoscope according to claim 1, wherein the cooling element has an electrically insulating coating.

10. The video endoscope according to claim 1, wherein:
the cooling element further has third and the fourth grooves; and
the first and second edges of the first flexible circuit board are disposed in first and second grooves and the first and second edges of the second flexible circuit board are disposed in third and fourth grooves.

* * * * *